(12) United States Patent
Slater et al.

(10) Patent No.: US 6,210,316 B1
(45) Date of Patent: Apr. 3, 2001

(54) RADIOACTIVE THERAPEUTIC SEEDS AND METHODS OF MAKING THE SAME

(75) Inventors: Charles R. Slater, Lauderdale; Scott L. Jahrmarkt, Miami Beach; Scott T. Smith, Miami, all of FL (US)

(73) Assignee: Syntheon, LLC, Miami, FL (US)

( * ) Notice: Subject to any disclaimer, the term of this patent is extended or adjusted under 35 U.S.C. 154(b) by 0 days.

(21) Appl. No.: 09/133,072

(22) Filed: Aug. 12, 1998

(51) Int. Cl.$^7$ .................................................. A61N 5/00
(52) U.S. Cl. ...................................................... 600/8
(58) Field of Search ............................................ 600/1–8

(56) References Cited

U.S. PATENT DOCUMENTS 5,924,974 * 7/1999 Loffler ....................................... 600/3

* cited by examiner

*Primary Examiner*—John P. Lacyk
(74) *Attorney, Agent, or Firm*—David P. Gordon; David S. Jacobson; Thomas A Gallagher

(57) ABSTRACT

Radioactive therapeutic seeds include a seed capsule, a radioactive isotope, and a radiopaque marker. According to one embodiment of the invention, the radiopaque marker is a silver wire coil and the isotope is coated on the surface of the coil. According to a first method of the invention, the therapeutic dosage of the seed is adjusted during manufacture by expanding or contracting the coil before it sized and deposited in the capsule. According to second embodiment, the radiopaque marker is a silver rod and the isotope is coated on a radiotransparent coil which is placed over the rod. According to a third embodiment, the isotope is coated on a plurality of rings which are stacked on a radiopaque rod. According to a second method of the invention, the therapeutic dosage of the seed is adjusted during manufacture by stacking a mixture of radio-inactive rings with radioactive rings on the radiopaque rod before the capsule is sealed.

10 Claims, 2 Drawing Sheets

RADIOACTIVE THERAPEUTIC SEEDS AND METHODS OF MAKING THE SAME

BACKGROUND OF THE INVENTION

1. Field of the Invention

The invention relates to radioactive therapeutic seeds. More particularly, the invention relates to improved radioactive therapeutic seeds for the treatment of oncological and other medical conditions.

2. State of the Art

Radioactive seed therapy is a well known and well accepted medical procedure for the treatment of various oncological and other medical conditions. Seed therapy, also known as brachytherapy typically involves the implantation of fifty to one hundred tiny capsules (seeds) into or around a treatment site. The capsules contain a radioactive isotope which irradiates the treatment site at close range without adversely affecting other parts of the body. Brachytherapy has been used successfully in the treatment of various types of cancers such as prostate cancer. It has also been used to prevent the growth or regrowth of tissues in the treatment of various occlusive diseases such as arteriosclerosis and arthrosclerosis subsequent to balloon angioplasty.

Radioactive therapeutic seeds are carefully designed to possess several important qualities. First, they must be relatively small, approximately 0.025 inch in diameter and approximately 0.16 inch long so that they may be implanted using minimally invasive instruments and techniques. Second, the radioactive isotope must be enclosed in a biocompatible protective package since the seeds are typically not removed and will remain in the body for many years. Third, each seed preferably includes a radiopaque marker so that it can be located at the treatment site with the aid of fluoroscopy. Fourth, the protective package and the radiopaque marker preferably do not cast "shadows" in the irradiation pattern of the isotope. Fifth, the isotope is preferably evenly distributed within the protective package so as to avoid any "hot spots" or "cold spots" of radiation. Sixth, the radiation energy or "activity" of the isotope must be carefully chosen so that the dosimetry or patient dosage of the seeds is predictable and controlled over the radioactive life of the seeds.

The state of the art of radioactive therapeutic seeds is substantially disclosed in seven U.S. patents: U.S. Pat. No. 5,713,828 to Coniglione for "Hollow-Tube Brachytherapy Device", U.S. Pat. No. 5,405,309 to Carden, Jr. for "X-Ray Emitting Interstitial Implants", U.S. Pat. No. 4,891,165 to Suthanthiran for "Device and Method for Encapsulating Radioactive Materials" and U.S. Pat. No. 4,784,116 to Russell, Jr. et al. for "Capsule for Interstitial Implants", U.S. Pat. No. 4,702,228 to Russell, Jr. et al. for "X-Ray Emitting Interstitial Implants", U.S. Pat. No. 4,323,055 to Kubiatowicz for "Radioactive Iodine Seed", and U.S. Pat. No. 3,351,049 to Lawrence for "Therapeutic Metal Seed Containing within a Radioactive Isotope Disposed on a Carrier and Method of Manufacture".

The Lawrence patent, which issued in 1967, describes many of the essential features of radioactive therapeutic seeds. Lawrence describes radioactive isotopes (I-125, Pd-103, Cs-131, Xe-133, and Yt-169) which emit low energy X-rays and which have relatively short half-lives. When implanted at a treatment site, these isotopes provide sufficient radiotherapy without posing a radiation danger to the medical practitioner(s), people in the vicinity of the patient, or other parts of the patient's body. Lawrence further describes a protective capsule which contains the isotope and prevents it from migrating throughout the body where it might interfere with healthy tissue. The capsule is cylindrical and made of low atomic number (low Z) biocompatible materials such as stainless steel or titanium which do not absorb X-rays. The isotope is coated on a rod shaped carrier made of similar X-ray transparent (or translucent) material and is placed inside the capsule cylinder. The ends of the capsule cylinder are closed by swaging or spinning and soldering or welding. According to a preferred embodiment, Lawrence places a radiopaque marker inside the seed. In one embodiment, the marker is a wire embedded inside the carrier rod. The wire is made of high atomic number (high Z) material such as gold or tungsten which absorb X-rays.

In 1980, Kubiatowicz made a minor improvement in the basic Lawrence design by providing that the entire isotope carrier be made of radiopaque material such as silver. Kubiatowicz recognized that since the isotope was carried on the entire outer surface of the carrier, there was no need to make the carrier body X-ray transparent as suggested by Lawrence. The larger radiopaque carrier body described by Kubiatowicz makes the seeds easier to see with X-ray or fluoroscopic examination. Thus, the seeds may be placed more accurately at/around the treatment site.

Several years later, Russell, Jr. et al., in U.S. Pat. Nos. 4,707,228 and 4,784,116, explained that the capsule design of Lawrence and Kubiatowicz produces anisotropic angular radiation distribution. According to Russell, Jr. et al., the shell forming techniques used in the Lawrence-type seeds results in large beads of shell material at the ends of the seeds. These beads substantially shield radiation thereby casting shadows in the irradiation pattern of the isotope. Russell, Jr. et al. proposed a new seed design to solve this problem. In particular, Russell, Jr. et al. proposed a seed having a cylindrical container which is sealed with end caps which have a wall thickness that is substantially the same as the wall thickness of the cylindrical container. The end caps are attached to the cylindrical container by welding or crimping.

An alternate solution to the non-uniform radiation pattern of the Lawrence-type seeds was proposed by Suthanthiran in U.S. Pat. No. 4,891,165. Suthanthiran's solution was to form a seed capsule from two interfitting sleeves, each having one open end and one closed end. The thickness of the sleeve side walls and their closed ends is such that when the sleeves are interfitted the total side wall thickness of the assembled capsule is approximately equal to the end wall thickness.

Other improvements in radioactive therapeutic seeds are disclosed in U.S. Pat. No. 5,405,309 which describes a safe isotopically pure Pd-103 seed, and U.S. Pat. No. 5,713,828 which describes a hollow tube seed which can be implanted with suture material.

Despite the fact that radioactive therapeutic seeds have been in use for over thirty years and despite the several significant improvements made in these seeds, many concerns still exist regarding their design and construction.

While significant attention has been given to the methods by which a cylindrical seed capsule is sealed, it is still difficult to seal the ends of such a small cylindrical capsule without adversely affecting the effective radiation dosimetry of the seed. Moreover, given the size of the seeds, it is very difficult to perform any welding of the capsules without adversely affecting the contents in some way.

While it is well known that the radioactive therapeutic seeds have virtually no shelf-life due to the relatively short half-life of the isotope used, little if any attention has been given to how this affects seed design and the manufacturing process. In particular, when seeds are manufactured from a stock pile of isotope, the first manufactured seeds will have a higher apparent radioactivity level than the last manufactured seeds. It is important for the practitioner to know the effective therapeutic dose contained in each seed and it is preferable that each seed have a predictable and consistent level of radioactivity.

SUMMARY OF THE INVENTION

It is therefore an object of the invention to provide radioactive therapeutic seeds and methods for manufacturing them whereby the apparent radioactivity level of each seed can be carefully predicted and controlled.

It is also an object of the invention to provide radioactive therapeutic seeds and methods for manufacturing them whereby the contents of the seed capsule are protected from welding heat during manufacture.

In accord with these objects which will be discussed in detail below, the radioactive therapeutic seeds of the present invention include a seed capsule, a radioactive isotope, and a radiopaque marker. According to one embodiment, the radiopaque marker is a silver wire coil and the isotope is coated on the surface of the coil. According to a first method of the invention, the apparent radioactivity level of the seed is adjusted during manufacture by expanding or contracting the coil before it is sized and deposited in the capsule. According to a second embodiment, the radiopaque marker is a silver rod and the isotope is coated on a radiotransparent coil which is placed over the rod. According to a third embodiment, the isotope is coated on a plurality of rings which are stacked on a radiopaque rod. According to a second method of the invention, the apparent radioactivity level of the seed is adjusted during manufacture by stacking a mixture of radio-inactive rings with radioactive rings on the radiopaque rod before the capsule is sealed. The radioactive rings are preferably made from a polymer tube having an interior coated with isotope.

According to a presently preferred embodiment, the capsule tube is made of very thin titanium or stainless steel with rotary swaged ends welded shut. Since the wall thickness is very thin (approximately 0.002 inches), a supporting structure of aluminum or other low Z material is placed inside the capsule and a silver wire coil coated with isotope is placed inside the supporting structure.

Additional objects and advantages of the invention will become apparent to those skilled in the art upon reference to the detailed description taken in conjunction with the provided figures.

DETAILED DESCRIPTION OF THE PREFERRED EMBODIMENTS

Figure 1:
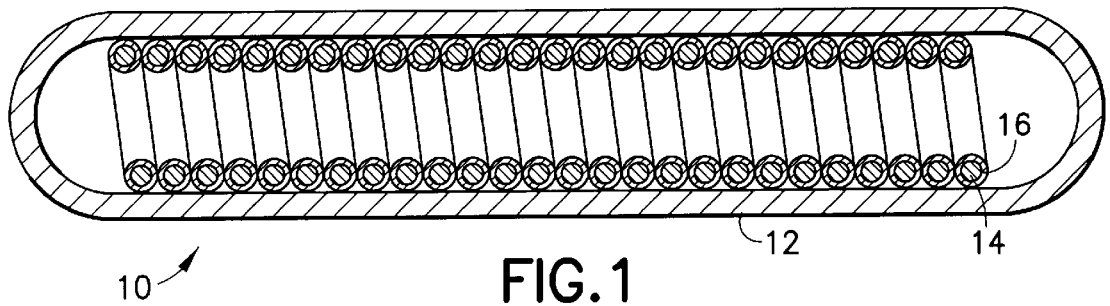
FIG. 1 is an enlarged schematic longitudinal section of a radioactive therapeutic seed according to a first embodiment of the invention.
Figure 2:
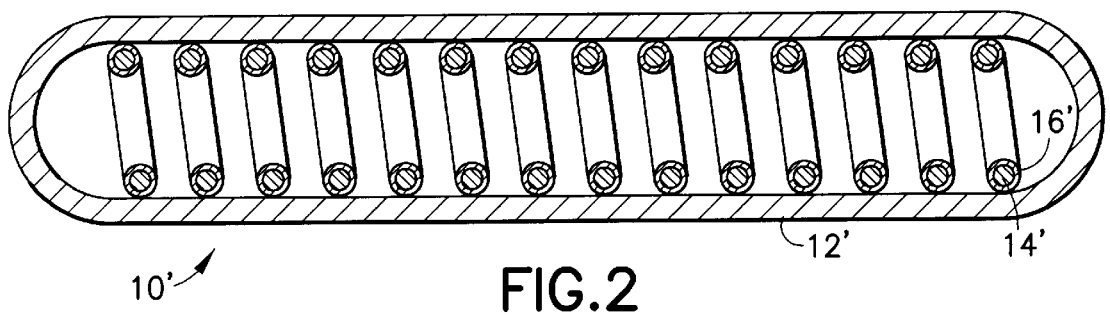
FIG. 2 is a view similar to FIG. 1 illustrating how the dosage level of the seed is reduced.

Referring now to FIGS. 1 and 2, a radioactive therapeutic seed 10 (10') according to a first embodiment of the invention includes a biocompatible capsule 12 (12') containing a silver wire coil 14 (14') which is coated with a radioactive isotope 16 (16'). The capsule 12 (12') may be configured according to any of the prior art patents described above, may be configured according to co-owned co-pending applications Ser. Nos. 09/133,081 and 09/133,082, now U.S. Pat. Nos. 6,080,099 and 6,007,475, respectively, which were filed simultaneously herewith, or may be configured according to a presently preferred embodiment described below with reference to FIG. 6. The use of a silver wire coil facilitates manufacture and is economical. Silver wire is inexpensive, easy to wind into a coil, and it easy to coat with isotope before or after winding. In addition, it is easy to cut wound silver coils to lengths for deposit into a seed capsule.

According to a first method of the invention, the quantity of radioactive isotope contained in the capsule 12 (12') is easily metered during manufacture of the seed 10 (10') by stretching or compressing the wire coil 14 (14') so that fewer or more turns of the coil reside in capsule 12 (12'). For example, the seed 10' shown in FIG. 2 is identical to the seed 10 except that the coil 14' has half as many turns as the coil 14. The amount of isotope 16' contained in the capsule 12' is thus approximately one half the amount of isotope 16 contained in the capsule 12. The stretching of the coil 14' allows half as much isotope 16' to be evenly distributed throughout the capsule 12'.

It will be appreciated that once the isotope coated silver wire is manufactured, its radioactivity begins to diminish according to the half-life of the isotope. It will also be appreciated that the seeds, once manufactured, are used almost immediately. In practice, it may take several weeks to deplete a batch of isotope coated silver wire. Thus, seeds which are manufactured and used shortly after the isotope coated silver wire is manufactured will have a higher apparent radioactivity level than seeds which are manufactured and used several weeks after the isotope coated silver wire is manufactured.

According to the invention, seeds which are manufactured soon after the isotope coated silver wire is manufactured will contain less isotope coated silver wire than seeds which are manufactured several weeks (e.g., one half-life later) after the isotope coated silver wire is manufactured. Therefore, the seed 10' in FIG. 2 is representative of an "early" batch of seeds, whereas the seed 10 in FIG. 1 is representative of "late" (one half-life late) batch of seeds containing twice as much isotope (but approximately the same total radioactivity) as the seeds of the early batch.

Figure 3:
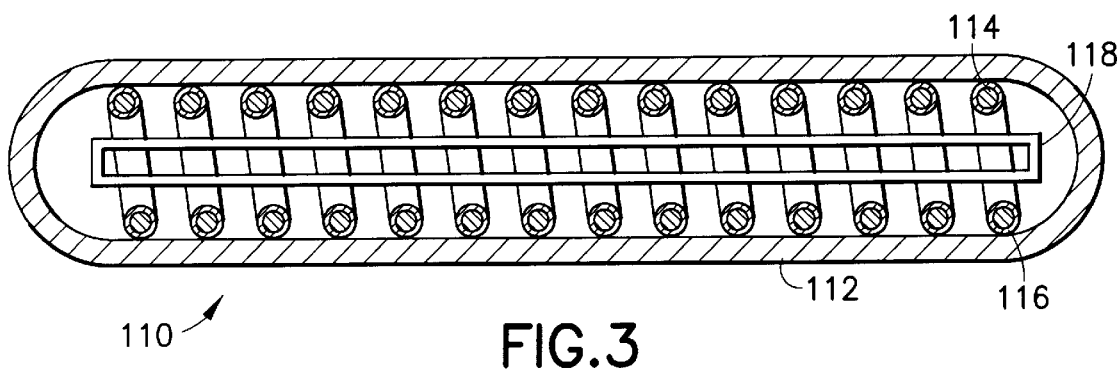
FIG. 3 is a view similar to FIG. 2 of a second embodiment of the invention.

Referring now to FIG. 3, a radioactive therapeutic seed 110 according to a second embodiment of the invention includes a biocompatible capsule 112 containing a radiotransparent coil 114 made of e.g., a low Z metal, plastic, or other low Z material which is coated with a radioactive isotope 116. A radiopaque marker is disposed inside the coil 114. The marker 118 may be a silver (or other high Z metal) wire or a rod of any desired material coated with a radiopaque material, etc. This embodiment allows for the selective manufacture of seeds with and without markers from the same batch of isotope coated material. The coiled material 114 in this embodiment may also be stretched or compressed to adjust the radioactivity of the seed as described above.

Figure 4:
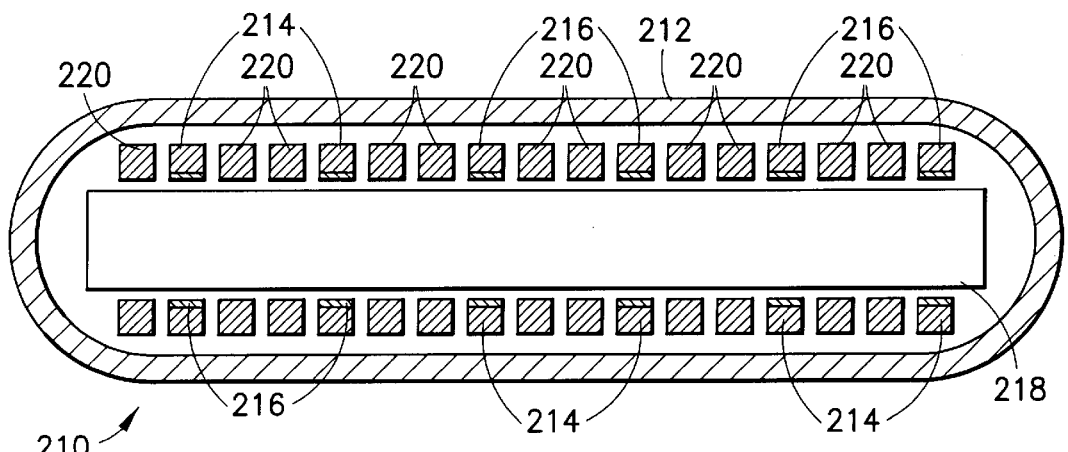
FIG. 4 is an enlarged schematic longitudinal section of a radioactive therapeutic seed according to a third embodiment of the invention illustrating a configuration for an early production batch.
Figure 5:
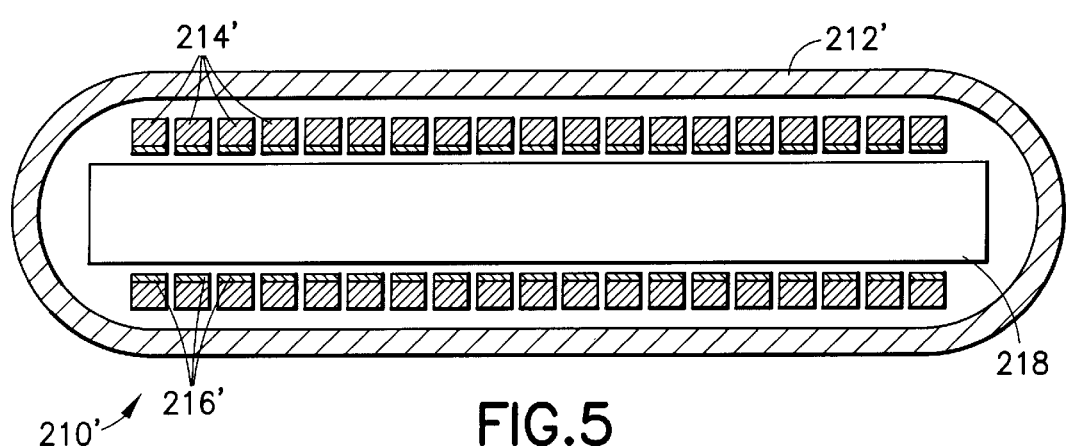
FIG. 5 is a view similar to FIG. 4 of the third embodiment illustrating a configuration for a late production batch.

Turning now to FIGS. 4 and 5, a radioactive therapeutic seed 210 (210') according to a third embodiment of the invention includes a biocompatible capsule 212, a plurality of radiotransparent (e.g. polymer) rings 214, each coated with isotope 216, mounted on a radiopaque rod 218, optionally with uncoated (radio-inactive) rings 220 interposed at regular intervals. As shown in FIG. 4, two of every three rings is radio-inactive and the radioactive rings 214 are spaced evenly along the marker rod 218, each separated from the other by two inactive rings. It will be appreciated that the seed 210 shown in FIG. 4 is representative of an "early" batch of seeds where the amount of isotope in the seed is less than "the full amount" which will be placed in seeds from a "late" batch. For example, the seed 210' shown in FIG. 5 has a "full amount" of radiotransparent rings 214', each coated with isotope 216', and no inactive rings are used. According to a presently preferred embodiment, the rings 214, 214' are made from a polymer tube which is coated with isotope on its inside surface and then sliced with a knife to form rings. Alternatively, the rings may be made from another low Z material.

Those skilled in the art will appreciate that the third embodiment may be modified so that each of the rings 214, 220 are radiopaque and the rod 218 may be either omitted or made of radiotransparent material. In such a case, the rings would be coated on their outside surface.

Figure 6:
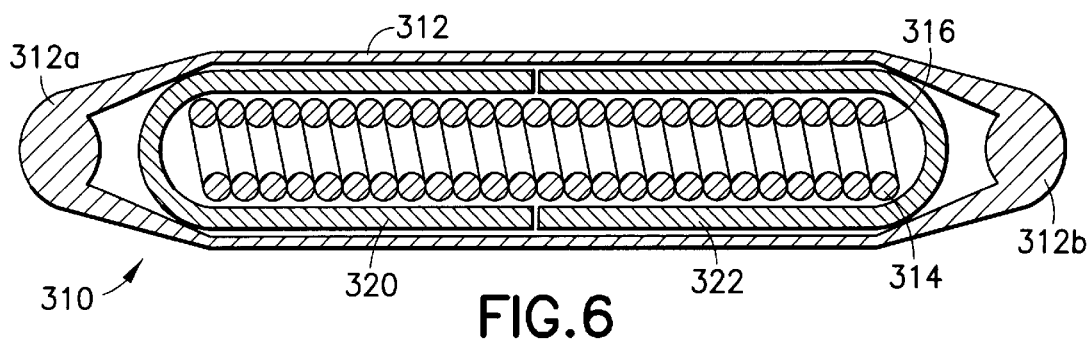
FIG. 6 is an enlarged schematic longitudinal section of a radioactive therapeutic seed according to a presently preferred embodiment of the invention.

Turning now to FIG. 6, a radioactive therapeutic seed 310 according to a presently preferred embodiment includes a capsule 312, a silver wire coil 314 bearing a radioactive coating 316, and a pair of radiotransparent or low Z material (e.g. aluminum) supporting members 320, 322. According to this embodiment, the capsule 312 is made of very thin (e.g. 0.002 inch) titanium or stainless steel with rotary swaged ends 312a, 312b welded shut. The supporting members 320, 322 dissipate welding heat and protect the capsule and its contents without absorbing any significant amount of radiation. This thin wall seed has a maximum radiation absorption of approximately 15% whereas the state of the art seeds have a minimum absorption of approximately 21%.

There have been described and illustrated herein several embodiments of a radioactive therapeutic seed. While particular embodiments of the invention have been described, it is not intended that the invention be limited thereto, as it is intended that the invention be as broad in scope as the art will allow and that the specification be read likewise. It will therefore be appreciated by those skilled in the art that yet other modifications could be made to the provided invention without deviating from its spirit and scope as so claimed.

What is claimed is:

1. A radioactive therapeutic seed, comprising:
   a) a biocompatible capsule; and
   b) a carrier structure carrying a radioactive isotope, said carrier structure disposed in said capsule, said carrier structure being one of a coil and a plurality of rings.

2. A seed according to claim 1, wherein:
   said carrier structure is a substantially radiopaque material.

3. A seed according to claim 2, wherein:
   said carrier structure is a wire coil.

4. A seed according to claim 1, wherein:
   said carrier structure is a substantially radiotransparent material.

5. A seed according to claim 4, further comprising:
   c) a radiopaque marker disposed inside said carrier structure.

6. A seed according to claim 1, wherein:
   said carrier structure is a plurality of rings coated with a radioactive isotope.

7. A seed according to claim 6, further comprising:
   c) a plurality of radio-inactive spacer rings interposed between said rings coated with a radioactive isotope.

8. A seed according to claim 1, further comprising:
   c) a support structure disposed in said capsule.

9. A seed according to claim 8, wherein:
   said support structure is a pair of tubes, each having an open end and a closed end, said open ends of said tubes facing each other.

10. A seed according to claim 8, wherein:
    said capsule is made of one of titanium and stainless steel, and
    said support structure is made of a substantially radiotransparent material.

* * * * *